(12) United States Patent
Bouix-Peter et al.

(10) Patent No.: US 9,102,607 B2
(45) Date of Patent: Aug. 11, 2015

(54) PEROXIDE DERIVATIVES, THEIR PROCESS OF PREPARATION AND THEIR USE IN HUMAN MEDICINE AND IN COSMETICS FOR THE TREATMENT OR PREVENTION OF ACNE

(75) Inventors: Claire Bouix-Peter, Vallauris (FR); Jean-Claude Pascal, Nice (FR); Nicolas Rodeville, Biot (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 22 days.

(21) Appl. No.: 13/514,579

(22) PCT Filed: Dec. 10, 2010

(86) PCT No.: PCT/EP2010/069418
§ 371 (c)(1),
(2), (4) Date: Sep. 4, 2012

(87) PCT Pub. No.: WO2011/070170
PCT Pub. Date: Jun. 16, 2011

(65) Prior Publication Data
US 2012/0323035 A1 Dec. 20, 2012

(30) Foreign Application Priority Data
Dec. 10, 2009 (FR) ...................... 09 58846

(51) Int. Cl.
| | | |
|---|---|---|
| *A61K 31/075* | (2006.01) | |
| *C07C 69/035* | (2006.01) | |
| *C07C 409/34* | (2006.01) | |
| *A61K 8/38* | (2006.01) | |
| *A61K 8/42* | (2006.01) | |
| *A61Q 19/00* | (2006.01) | |
| *C07C 409/40* | (2006.01) | |

(52) U.S. Cl.
CPC ............... *C07C 409/34* (2013.01); *A61K 8/38* (2013.01); *A61K 8/42* (2013.01); *A61Q 19/00* (2013.01); *C07C 409/40* (2013.01); *C07C 2101/02* (2013.01); *C07C 2101/04* (2013.01); *C07C 2101/08* (2013.01); *C07C 2101/14* (2013.01); *C07C 2103/74* (2013.01)

(58) Field of Classification Search
CPC ............. C07C 409/32; C07C 2101/14; C07C 2103/74; A61Q 19/00; A61K 8/38
See application file for complete search history.

(56) References Cited

U.S. PATENT DOCUMENTS

| | | |
|---|---|---|
| 3,075,921 A | 1/1963 | Brocklehurst et al. |
| 4,355,028 A | 10/1982 | Kligman et al. |
| 4,364,940 A | 12/1982 | Neiss et al. |
| 4,446,145 A | 5/1984 | Van Bever |
| 4,514,385 A | 4/1985 | Damani et al. |
| 4,520,133 A * | 5/1985 | Dines et al. .................. 514/568 |
| 4,767,750 A | 8/1988 | Jacquet et al. |
| 5,137,923 A | 8/1992 | Philippe et al. |
| 5,409,917 A | 4/1995 | Robinson et al. |
| 5,439,923 A | 8/1995 | Cullinan |
| 2002/0121221 A1 | 9/2002 | Baettig |

FOREIGN PATENT DOCUMENTS

| | | |
|---|---|---|
| EP | 0 052 705 A1 | 6/1982 |
| EP | 0 563 813 A1 | 10/1993 |
| EP | 1 219 682 A1 | 7/2002 |
| FR | 2 581 542 A1 | 11/1986 |
| FR | 2 607 498 A1 | 6/1988 |
| GB | 1 054 124 | 1/1967 |
| GB | 2 088 717 A | 6/1982 |
| GB | 2 090 135 A | 7/1982 |

OTHER PUBLICATIONS

Evanochko et al, Journal of Organic Chemistry, Investigation of o-Acetoxyaryl Radicals, 1979, 44(24), pp. 4426-4430.*
Wasdo, Topical Delivery of a Model Phenolic Compound:Alkyloxycarbonyl Prodrugs of Acetaminophen, 2005, Ph. D. thesis, University of Florida, pp. i-125.*
Evanochko et al., "Investigation of o-Acetoxyaryl Radicals," J. Org. Chem., 1979, pp. 4426-4430, vol. 44, No. 24.
Written Opinion of the International Searching Authority issued on Jun. 12, 2012, in International Patent Application No. PCT/EP2010/069418.

* cited by examiner

*Primary Examiner* — Paul A Zucker
(74) *Attorney, Agent, or Firm* — Dentons US LLP

(57) ABSTRACT

Compounds of the following general formula (I):

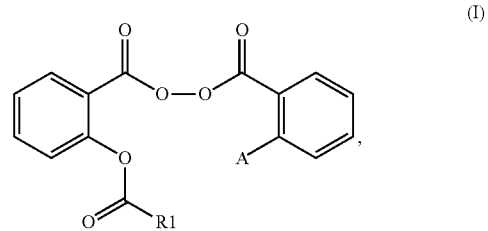

are described.
Also described, are processes of their preparation and their use in therapeutic applications.

10 Claims, No Drawings

PEROXIDE DERIVATIVES, THEIR PROCESS OF PREPARATION AND THEIR USE IN HUMAN MEDICINE AND IN COSMETICS FOR THE TREATMENT OR PREVENTION OF ACNE

CROSS-REFERENCE TO PRIOR APPLICATIONS

This application is a National Stage of PCT/EP2010/069418, filed Dec. 10, 2010, and designating the United States (published in the English language on Jun. 16, 2011, as WO 2011/070170 A1; the title and abstract were also published in English), which claims priority of FR 0958846, filed Dec. 10, 2009, each hereby expressly incorporated by reference in its entirety and each assigned to the assignee hereof.

Acne affects 90% of all adolescents but also men and women aged from about twenty to about thirty years, or it can even persist throughout adulthood. The process of development of acne has been described by W. J. Cunliffe in 'New Approaches to Acne Treatment', published by Martin Dunitz, London, 1989.

Acne vulgaris is a chronic disorder of the pilosebaceous follicles (apparati) which is characterized by comedones (blackheads), papules, pustules, cysts, nodules and often scars which appear in the most visible regions of the skin, in particular the face, chest, back and sometimes the neck and top of the arms.

The pilosebaceous apparatus is largely placed under the control of endogenous hormones (mainly androgens) which are present at unusually high concentrations in the blood during adolescence and puberty and are reflected by an excessive production of sebum. This state of affairs can worsen due to a concomitant increase in the degree of keratinization of the cornea layer of the skin (stratum corneum). As the horny cells proliferate, they can form an occlusive plug or comedo which, in combination with the increased production of sebum, constitutes an ideal medium for the proliferation of the strains resident in the skin, such as the Gram positive anaerobic bacterium *Propionibacterium acnes*.

The exposed follicles may assume a dark colour due to the deposition of pigment originating from the damaged cells of the deep layer of the skin.

Acne is a condition comprising several stages and, in its severest form, results in the hospitalization of the patient and significant discomfort with the long-term presence of skin scars.

There exists a need for improved treatments of acne which effectively prevent the condition from evolving towards its severest form and which can be used without unfavourable effects by the majority of the people affected.

Many treatments are currently available for treating acne but each treatment unfortunately has limits which it would be desirable to overcome.

In the majority of cases, the treatment of acne involves topical formulations in the form of creams, gels, emulsions or lotions comprising chosen agents.

These agents comprise, for example, hormones or hormone agonists and antagonists (EPA1 0 563 813 and U.S. Pat. No. 5,439,923), antimicrobial agents (U.S. Pat. No. 4,446,145, GB 2 088 717, GB 2 090 135, GB 1 054 124 and U.S. Pat. No. 5,409,917) or salicylic acid (U.S. Pat. No. 4,514,385, U.S. Pat. No. 4,355,028, EPA1 0 052 705, FR-A 2 581 542 and FR-A 2 607 498).

The problems associated with the topical treatment of acne using creams, gels, emulsions or lotions comprise the lack of preciseness of the application and the absence of precise control of the dose at the site targeted. The application of a cream, of a gel, of an emulsion or of a lotion is reflected by the exposure of a surface area considerably greater than that covered by the lesion, which has the effect of exposing normal healthy skin to the antiacne formulation. Thus, for example, salicylic acid is irritating to normal skin in the case of prolonged exposure, in particular at high concentrations.

The administration by the oral route of antiacne agents is commonly provided in severe cases of acne. These have been reviewed by Sykes N. I. and Webster G. in 'Acne, A Review of Optimum Treatment', Drugs, 48, 59-70 (1994). Numerous side effects have been described in the context of the administration of antiacne active compounds by the oral route.

Thus, for example, isotretinoin, which is a vitamin A derivative, exhibits associated risks of teratogenicity and it can constitute a risk to women of reproductive age.

The oral administration of antibiotics suitable for the treatment of acne can be accompanied by the appearance of side effects, such as abdominal cramps, glossophytia, coughing, diarrhoea, fatigue, buccal irritation and other undesirable symptoms.

There thus exists a clear medical and cosmetic need for the treatment of the related conditions and pathologies.

In this context, the present invention proposes to provide novel peroxide derivatives having a better antiacne effectiveness resulting, for example, from a better bactericidal activity than the compounds of the prior art, such as benzoyl peroxide, while controlling the potential sensitizing effect and the irritant effect and while not adding an antiinflammatory activity component.

A subject-matter of the present invention is compounds of following general formula (I):

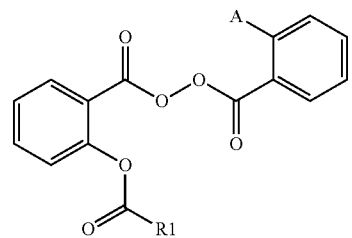

in which:

R1 represents a lower alkyl, a higher alkyl, a cycloalkyl, a cycloalkylalkyl, a lower alkoxy, a higher alkoxy, a cycloalkyloxy, a cycloalkylalkoxy, an aryl, an aryloxy or a mono- or dialkylamino;

A represents a hydrogen or the following sequence:

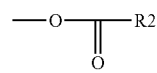

R2 represents a lower alkoxy, a higher alkoxy, a cycloalkyloxy, a cycloalkylalkoxy, an aryloxy or a mono- or dialkylamino.

According to the present invention, the preferred compounds corresponding to the general formula (I) are those which exhibit the following characteristics:

—R1 represents a lower alkyl, a cycloalkyl, a cycloalkylalkyl, a lower alkoxy, a cycloalkyloxy or a mono- or dialkylamino;

A represents a hydrogen or a defined group of such type:

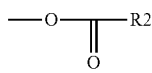

—R2 represents a lower alkoxy, a cycloalkyloxy or a mono- or dialkylamino.

Still according to the present invention, the particularly preferred compounds corresponding to the general formula (I) are those for which:
—R1 represents a lower alkyl, a cycloalkyl, a cycloalkylalkyl, a lower alkoxy or a cycloalkyloxy;
A represents a hydrogen or a defined group of such type:

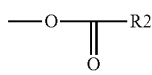

—R2 represents a lower alkoxy or a cycloalkyloxy.

According to the present invention, the term "a lower alkyl" denotes a saturated and linear or branched hydrocarbon chain comprising from 2 to 4 carbon atoms.

According to the present invention, the term "a higher alkyl" denotes a saturated and linear or branched hydrocarbon chain comprising from 5 to 10 carbon atoms.

According to the present invention, the term "a cycloalkyl" denotes a saturated and cyclic, bicyclic or tricyclic hydrocarbon chain comprising from 3 to 10 carbon atoms.

According to the present invention, the term "a cycloalkylalkyl" denotes an alkyl substituted by a cycloalkyl.

According to the present invention, the term "a lower alkoxy" denotes an oxygen atom substituted by a lower alkyl.

According to the present invention, the term "a higher alkoxy" denotes an oxygen atom substituted by a higher alkyl.

According to the present invention, the term "an aryl" denotes an unsubstituted phenyl or naphthyl.

According to the present invention, the term "an aryloxy" denotes an oxygen atom substituted by an aryl.

According to the present invention, the term "a cycloalkylalkoxy" denotes an oxygen atom substituted by a cycloalkyl (lower alkyl).

According to the present invention, the term "a cycloalkoxy" denotes an oxygen atom substituted by a cycloalkyl.

According to the present invention, the term "a mono- or dialkylamino" denotes an amino substituted by one or two identical or different lower alkyls.

Mention may in particular be made, among the compounds of general formula (I) coming within the scope of the present invention, of the following:
Example 1: (2-(Ethoxycarbonyloxy)benzoyl)benzoyl peroxide
Example 2: (2-(tert-Butoxycarbonyloxy)benzoyl)benzoyl peroxide
Example 3: Bis(2-(ethoxycarbonyloxy)benzoyl)peroxide
Example 4: Bis(2-(tert-butoxycarbonyloxy)benzoyl)peroxide
Example 5: (2-(Isopropoxycarbonyloxy)benzoyl)benzoyl peroxide
Example 6: Bis(2-(isopropoxycarbonyloxy)benzoyl)peroxide
Example 7: (2-(Cyclohexyloxycarbonyloxy)benzoyl)benzoyl peroxide
Example 8: Bis(2-(cyclohexyloxycarbonyloxy)benzoyl)peroxide
Example 9: (2-(tert-Butyryloxy)benzoyl)benzoyl peroxide
Example 10: (2-(Isobutyryloxy)benzoyl)benzoyl peroxide
Example 11: (2-(Cyclohexanecarbonyloxy)benzoyl)benzoyl peroxide
Example 12: [2-(2-(Adamantan-1-yl)acetoxy)benzoyl]benzoyl peroxide
Example 13: [2-(Adamentene-1-carbonyloxy)benzoyl]benzoyl peroxide
Example 14: (2-(Phenoxycarbonyloxy)benzoyl)benzoyl peroxide
Example 15: (2-(Methoxycarbonyloxy)benzoyl)benzoyl peroxide
Example 16: (2-(Propoxycarbonyloxy)benzoyl)benzoyl peroxide
Example 17: (2-(Butoxycarbonyloxy)benzoyl)benzoyl peroxide
Example 18: (2-(sec-Butoxycarbonyloxy)benzoyl)benzoyl peroxide
Example 19: (2-(Isobutoxycarbonyloxy)benzoyl)benzoyl peroxide
Example 20: (2-(Propionyloxy)benzoyl)benzoyl peroxide
Example 21: (2-(Butyryloxy)benzoyl)benzoyl peroxide
Example 22: (2-(Pentanoyloxy)benzoyl)benzoyl peroxide
Example 23: [2-(3-Methylbutyryloxy)benzoyl]benzoyl peroxide
Example 24: [2-(2-Methylbutyryloxy)benzoyl]benzoyl peroxide
Example 25: (2-(Cyclopropanecarbonyloxy)benzoyl)benzoyl peroxide
Example 26: (2-(Cyclobutanecarbonyloxy)benzoyl)benzoyl peroxide
Example 27: (2-(Cyclopentanecarbonyloxy)benzoyl)benzoyl peroxide
Example 28: (2-(Benzoyloxy)benzoyl)benzoyl peroxide
Example 29: (2-(Dimethylcarbamoyloxy)benzoyl)benzoyl peroxide
Example 30: (2-(Diethylcarbamoyloxy)benzoyl)benzoyl peroxide
Example 31: (2-(Methylcarbamoyloxy)benzoyl)benzoyl peroxide
Example 32: (2-(Ethylcarbamoyloxy)benzoyl)benzoyl peroxide
Example 33: (2-(Isopropylcarbamoyloxy)benzoyl)benzoyl peroxide
Example 34: (2-(Propylcarbamoyloxy)benzoyl)benzoyl peroxide
Example 35: [2-((Isopropyl)(methyl)carbamoyloxy)-benzoyl]benzoyl peroxide
Example 36: [2-((Ethyl)(isopropyl)carbamoyloxy)benzoyl]benzoyl peroxide
Example 37: (2-(Hexanoyloxy)benzoyl)benzoyl peroxide
Example 38: (2-(Heptanoyloxy)benzoyl)benzoyl peroxide
Example 39: (2-(Octanoyloxy)benzoyl)benzoyl peroxide
Example 40: (2-(Nonanoyloxy)benzoyl)benzoyl peroxide
Example 41: [2-(2-Ethylbutyryloxy)benzoyl]benzoyl peroxide
Example 42: [2-(3,3-Dimethylbutyryloxy)benzoyl]benzoyl peroxide
Example 43: (2-(Pentyloxycarbonyloxy)benzoyl)benzoyl peroxide
Example 44: (2-(Hexyloxycarbonyloxy)benzoyl)benzoyl peroxide
Example 45: (2-(Heptyloxycarbonyloxy)benzoyl)benzoyl peroxide Example 46: (2-(Octyloxycarbonyloxy)benzoyl)benzoyl peroxide
Example 47: [2-(1-Ethylpropoxycarbonyloxy)benzoyl]benzoyl peroxide
Example 48: [2-(2,2-Dimethylpropoxycarbonyloxy)benzoyl]benzoyl peroxide
Example 49: Bis(2-(phenoxycarbonyloxy)benzoyl)peroxide
Example 50: Bis(2-(methoxycarbonyloxy)benzoyl)peroxide
Example 51: Bis(2-(propoxycarbonyloxy)benzoyl)peroxide
Example 52: Bis(2-(butoxycarbonyloxy)benzoyl)peroxide
Example 53: Bis[2-(3-methylbutyryloxy)benzoyl]peroxide
Example 54: Bis[2-(2-methylbutyryloxy)benzoyl]peroxide
Example 55: Bis(2-(dimethylcarbamoyloxy)benzoyl)peroxide
Example 56: Bis(2-(diethylcarbamoyloxy)benzoyl)peroxide
Example 57: Bis(2-(methylcarbamoyloxy)benzoyl)peroxide
Example 58: Bis(2-(ethylcarbamoyloxy)benzoyl)peroxide
Example 59: Bis(2-(isopropylcarbamoyloxy)benzoyl)peroxide
Example 60: Bis(2-propylcarbamoyloxy)benzoyl)peroxide
Example 61: Bis(2-((isopropyl)(methyl)carbamoyloxy)-benzoyl)peroxide
Example 62: Bis(2-((ethyl)(isopropyl)carbamoyloxy)-benzoyl)peroxide
Example 63: Bis(2-(pentyloxycarbonyloxy)benzoyl)peroxide
Example 64: Bis(2-(hexyloxycarbonyloxy)benzoyl)peroxide
Example 65: Bis(2-(heptyloxycarbonyloxy)benzoyl)peroxide
Example 66: Bis(2-(octyloxycarbonyloxy)benzoyl)peroxide
Example 67: Bis[2-(1-ethylpropoxycarbonyloxy)benzoyl] peroxide
Example 68: Bis[2-(2,2-dimethylpropoxycarbonyloxy)-benzoyl]peroxide
Example 69: (2-(Methoxycarbonyloxy)benzoyl)2-(isobutyryloxy)benzoyl peroxide
Example 70: (2-(Methoxycarbonyloxy)benzoyl)2-(tert-butyryloxy)benzoyl peroxide
Example 71: (2-(Methoxycarbonyloxy)benzoyl)2-(cyclohexanecarbonyloxy)benzoyl peroxide
Example 72: (2-(Methoxycarbonyloxy)benzoyl)2-(methylcarbamoyloxy)benzoyl peroxide
Example 73: (2-(Methoxycarbonyloxy)benzoyl)2-(dimethylcarbamoyloxy)benzoyl peroxide
Example 74: (2-(Ethoxycarbonyloxy)benzoyl)2-(isobutyryloxy)benzoyl peroxide
Example 75: (2-(Ethoxycarbonyloxy)benzoyl)2-(tert-butyryloxy)benzoyl peroxide
Example 76: (2-(Ethoxycarbonyloxy)benzoyl)2-(cyclohexanecarbonyloxy)benzoyl peroxide
Example 77: (2-(Ethoxycarbonyloxy)benzoyl)2-(methylcarbamoyloxy)benzoyl peroxide
Example 78: (2-(Ethoxycarbonyloxy)benzoyl)2-(dimethylcarbamoyloxy)benzoyl peroxide
Example 79: (2-(Isopropoxycarbonyloxy)benzoyl)2-(isobutyryloxy)benzoyl peroxide
Example 80: (2-(Isopropoxycarbonyloxy)benzoyl)2-(tert-butyryloxy)benzoyl peroxide
Example 81: (2-(Isopropoxycarbonyloxy)benzoyl)2-(cyclohexanecarbonyloxy)benzoyl peroxide
Example 82: (2-(Isopropoxycarbonyloxy)benzoyl)2-(methylcarbamoyloxy)benzoyl peroxide
Example 83: (2-(Isopropoxycarbonyloxy)benzoyl)2-(dimethylcarbamoyloxy)benzoyl peroxide
Example 84: (2-(tert-Butoxycarbonyloxy)benzoyl)2-(isobutyryloxy)benzoyl peroxide
Example 85: (2-(tert-Butoxycarbonyloxy)benzoyl)2-(tert-butyryloxy)benzoyl peroxide
Example 86: (2-(tert-Butoxycarbonyloxy)benzoyl)2-(cyclohexanecarbonyloxy)benzoyl peroxide
Example 87: (2-(tert-Butoxycarbonyloxy)benzoyl)2-(methylcarbamoyloxy)benzoyl peroxide
Example 88: (2-(tert-Butoxycarbonyloxy)benzoyl)2-(dimethylcarbamoyloxy)benzoyl peroxide
Example 89: (2-(Cyclohexyloxycarbonyloxy)benzoyl)2-(isobutyryloxy)benzoyl peroxide
Example 90: (2-(Cyclohexyloxycarbonyloxy)benzoyl)2-(tert-butyryloxy)benzoyl peroxide
Example 91: (2-(Cyclohexyloxycarbonyloxy)benzoyl)2-(cyclohexanecarbonyloxy)benzoyl peroxide
Example 92: (2-(Cyclohexyloxycarbonyloxy)benzoyl)2-(methylcarbamoyloxy)benzoyl peroxide
Example 93: (2-(Cyclohexyloxycarbonyloxy)benzoyl)2-(dimethylcarbamoyloxy)benzoyl peroxide
Example 94: (2-(Ethoxycarbonyloxy)benzoyl)2-(isopropoxycarbonyloxy)benzoyl peroxide
Example 95: (2-(Ethoxycarbonyloxy)benzoyl)2-(tert-butoxycarbonyloxy)benzoyl peroxide
Example 96: (2-(Ethoxycarbonyloxy)benzoyl)2-(cyclohexyloxycarbonyloxy)benzoyl peroxide
Example 97: (2-(tert-Butyryloxy)benzoyl)2-(cyclohexyloxycarbonyloxy)benzoyl peroxide A general description of methods for the preparation of compounds of formula (I) is given below. In these schemes and in the description of the process which will follow, all of the substituents are as defined for the compounds of formula (I), unless otherwise specified.

In the case where the group A defined in formula (I) is a hydrogen, the compounds of general formula (I) are prepared according to Reaction Scheme 1 or Reaction Scheme 2 presented below.

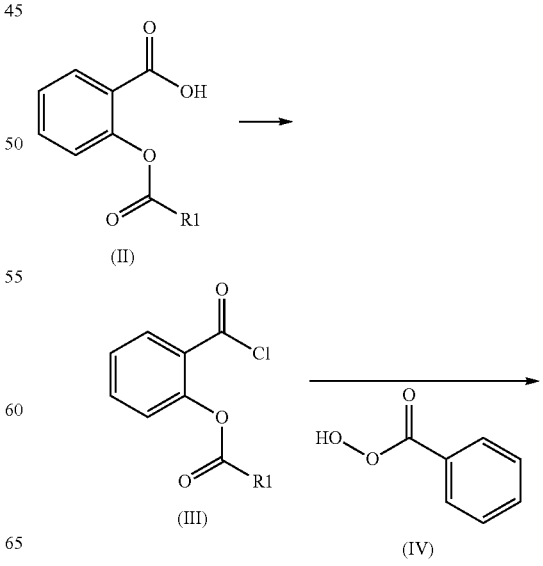

Scheme 1

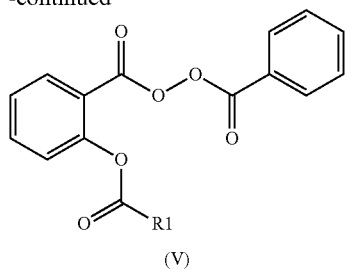

(V)

According to Scheme 1, the acid chlorides of general formula (III) are prepared from the carboxylic acid (II) by methods chosen from those known to a person skilled in the art (EP 121 968 2). They comprise the use of thionyl chloride and pyridine in a solvent, such as toluene or dichloromethane, for example.

The carboxylic acids of general formula (II) are available commercially or are prepared according to the methods described in Schemes 7 and 8.

In a final stage, the compounds of general formula (V) can be prepared by coupling between the acyl chlorides of formula (III) and the peracid of formula (IV) by using, as base, pyridine in a solvent mixture, such as dichloromethane and chloroform (Evanochko, W. T. and Shevlin, P. B.; *J. Org. Chem.*, 1979, 44(24), 4426-4430).

The peracid of general formula (IV) is prepared from benzoyl peroxide according to the method described in Scheme 11.

Scheme 2

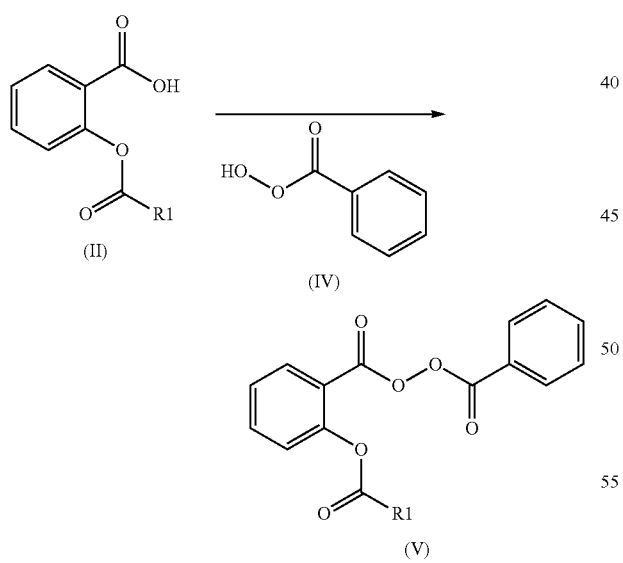

According to Scheme 2, the peroxides of general formula (V) are prepared by coupling between the carboxylic acids of formula (II) and the peracid of formula (IV) by using, for example, as coupling agent, N,N'-dicyclohexylcarbodiimide in a mixture of solvents, such as diethyl ether and dichloromethane (Spantulescu, M. D.; Jain, R. P.; Derksen, D. J. and Vederas, J. C.; *Org. Lett.*, 2003, 5(16), 2963-2965).

The carboxylic acids of general formula (II) are commercially available or are prepared according to the methods described in Schemes 7 and 8.

The peracid of general formula (IV) is prepared from benzoyl peroxide according to the method described in Scheme 11.

In the case where the group A defined in the formula (I) is not a hydrogen and where the group R2 is identical to the group R1, the compounds of general formula (I) are prepared according to Reaction Scheme 3 or Reaction Scheme 4 presented below.

Scheme 3

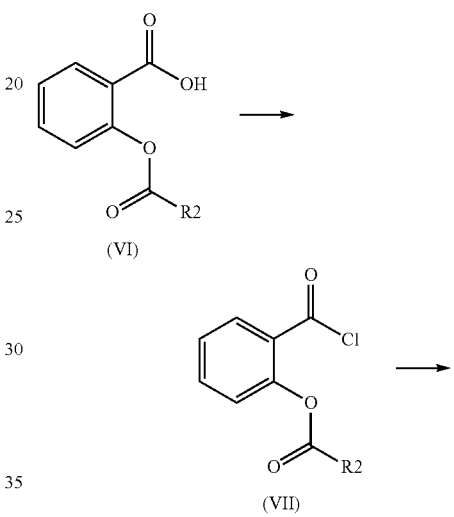

According to Scheme 3, the acid chlorides of general formula (VII) are prepared from the carboxylic acid (VI) by methods chosen from those known to a person skilled in the art (EP 121 968 2). They comprise the use of thionyl chloride and pyridine in a solvent, such as toluene or dichloromethane, for example.

The carboxylic acids of general formula (VI) are prepared according to the methods described in Schemes 9 and 10.

In a final stage, the compounds of general formula (VIII) can be prepared by coupling between two acyl chlorides of formula (VII) by methods chosen from those known to a person skilled in the art (EP 0 108 821). They comprise the use of hydrogen peroxide and sodium bicarbonate in a solvent, such as tetrahydrofuran, for example.

Scheme 4

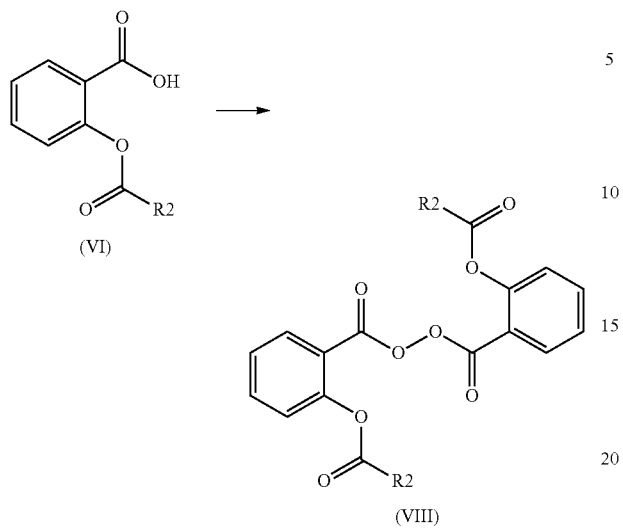

According to Scheme 4, the peroxides of general formula (VIII) are prepared by reaction between two carboxylic acids of formula (VI) by using, for example, as, N,N'-dicyclohexylcarbodiimide and hydrogen peroxide, for example in a mixture of solvents, such as diethyl ether and dichloromethane (Spantulescu, M. D.; Jain, R. P.; Derksen, D. J.; Vederas, J. C.; *Org. Lett.*, 2003, 5(16), 2963-2965).

The carboxylic acids of general formula (VI) are available commercially or are prepared according to the methods described in Schemes 9 and 10.

In the case where the group A defined in the formula (I) is not a hydrogen and where the group R2 is different from the group R1, the compounds of general formula (I) are prepared according to Reaction Scheme 5 and Reaction Scheme 6 presented below.

Scheme 5

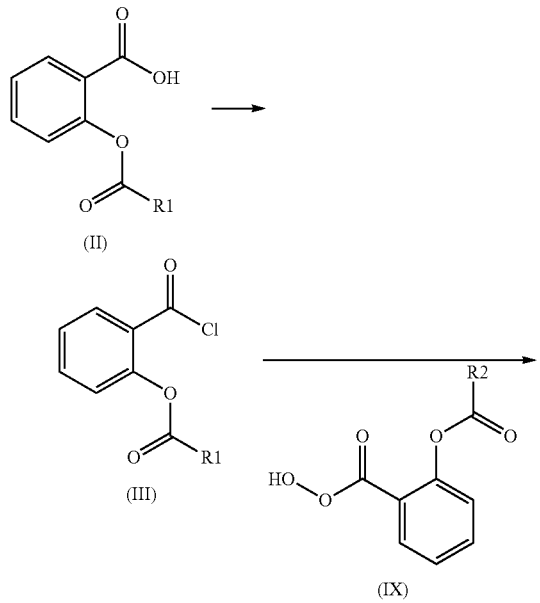

According to Scheme 5, the acid chlorides of general formula (III) are prepared from the carboxylic acid (II) by methods chosen from those known to a person skilled in the art (EP 121 968 2). They comprise the use of thionyl chloride and pyridine in a solvent, such as toluene or dichloromethane, for example.

The carboxylic acids of general formula (II) are commercially available or are prepared according to the methods described in Schemes 7 and 8.

In a final stage, the compounds of general formula (X) can be prepared by coupling between the acyl chlorides of formula (III) and the peracid of formula (IX) by using, as base, pyridine, for example in a mixture of solvents, such as dichloromethane and chloroform.

The peracid of general formula (IX) is prepared according to the method described in Scheme 12 starting from the peroxide of formula (VIII).

Scheme 6

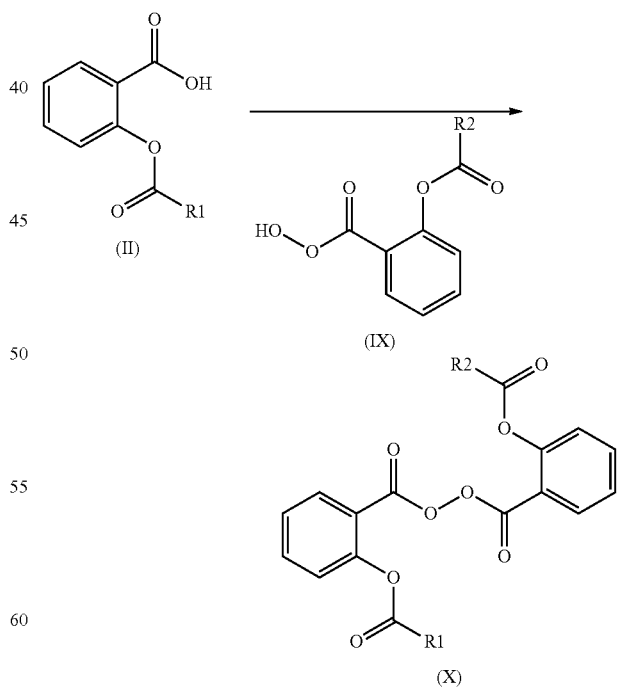

According to Scheme 6, the peroxides of general formula (X) are prepared by coupling between the carboxylic acids of formula (II) and the peracid of formula (IX) by using, for example, as coupling agent, N,N'-dicyclohexylcarbodiimide in a mixture of solvents, such as diethyl ether and dichloromethane, for example.

The carboxylic acids of general formula (II) are available commercially or are prepared according to the methods described in Schemes 7 and 8.

The peracid of general formula (IX) is prepared according to the method described in Scheme 12 starting from the defined peroxide of formula (VIII).

The carboxylic acids of formula (II) can be prepared according to Reaction Scheme 7 or 8.

Scheme 7

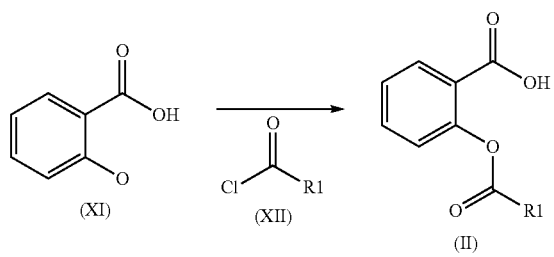

According to Scheme 7, the carboxylic acids of formula (II) are prepared from salicylic acid (XI) by methods chosen from those known to a person skilled in the art (Lima, S.; Kumar, S.; Gawandi, V.; Momany, C. and Phillips, R. S.; *J. Med. Chem.*, 2009, 52 (2), 389-396, and Sessions, E. H. and Jacobi, P. A.; *Org. Lett.*, 2006, 8(18), 4125-4128). They comprise the use of the acid chloride of formula (XII) and of bases, such as N,N-dimethylaniline, triethylamine or pyridine, in a solvent, such as toluene or dichloromethane, for example.

The acid chlorides of formula (XII) are available commercially.

Scheme 8

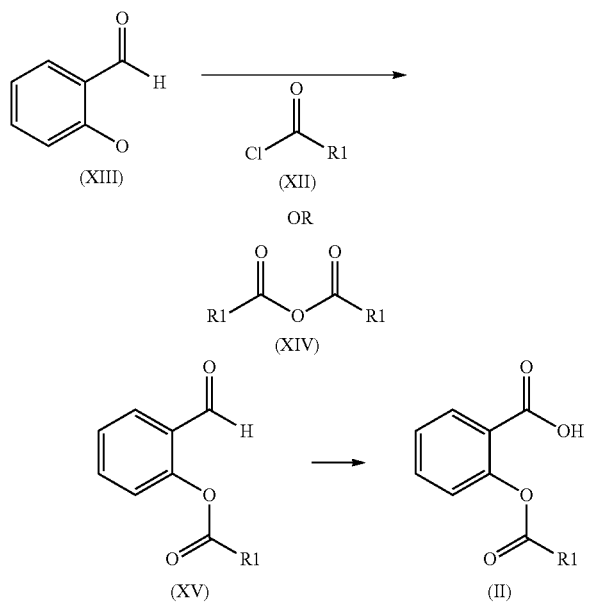

According to Scheme 8, the aldehydes of formula (XV) are prepared from salicylaldehyde (XIII) by methods chosen from those known to a person skilled in the art (Lima, S.; Kumar, S.; Gawandi, V.; Momany, C.; Phillips, R. S.; *J. Med. Chem.*, 2009, 52 (2), 389-396, and Sessions, E. H. and Jacobi, P. A.; *Org. Lett.*, 2006, 8(18), 4125-4128). They comprise the use of the acid chloride of formula (XII) or of anhydrides of formula (XIV) and of bases, such as triethylamine or pyridine, in a solvent, such as acetone or dichloromethane, for example.

In a final stage, the carboxylic acids of general formula (II) can be prepared by oxidation of the aldehydes of formula (XV) with sodium perchlorite in a mixture of solvents, such as water and tert-butanol (Marsini, M. A.; Gowin, K. M.; Pettus, T. R. R.; *Org. Lett.*, 2006, 8(16), 3481-3483).

The carboxylic acids of formula (VI) can be prepared according to Reaction Scheme 9 or 10.

Scheme 9

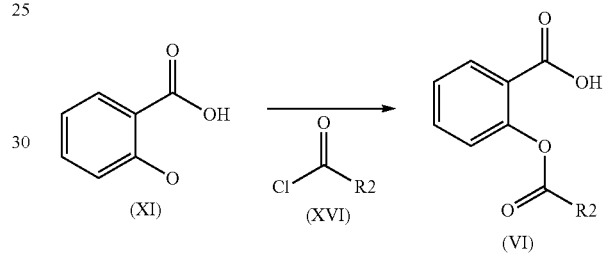

According to Scheme 9, the carboxylic acids of formula (VI) are prepared from salicylic acid (XI) by methods chosen from those known to a person skilled in the art (Lima, S.; Kumar, S.; Gawandi, V.; Momany, C.; Phillips, R. S.; *J. Med. Chem.*, 2009, 52 (2), 389-396, and Sessions, E. H. and Jacobi, P. A.; *Org. Lett.*, 2006, 8(18), 4125-4128). They comprise the use of the acid chloride of formula (XVI) and of bases, such as N,N-dimethylaniline, triethylamine or pyridine, in a solvent, such as toluene or dichloromethane, for example.

The acid chlorides of formula (XVI) are commercially available.

Scheme 10

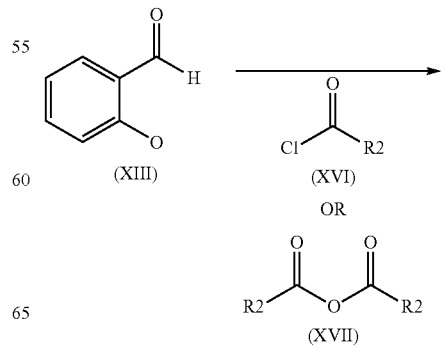

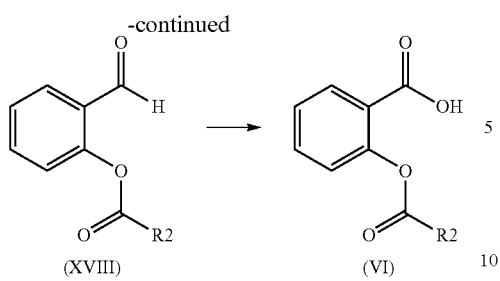

(XVIII) → (VI)

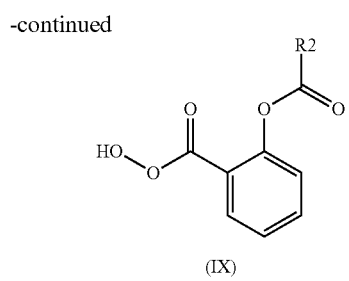

(IX)

According to Scheme 10, the aldehydes of formula (XVIII) are prepared from salicylaldehyde (XIII) by methods chosen from those known to a person skilled in the art (Lima, S.; Kumar, S.; Gawandi, V.; Momany, C.; Phillips, R. S.; *J. Med. Chem.* 2009, 52 (2), 389-396, and Sessions, E. H. and Jacobi, P. A.; *Org. Lett.,* 2006, 8(18), 4125-4128). They comprise the use of the acid chloride of formula (XVI) or of anhydrides of formula (XVII) and of bases, such as triethylamine or pyridine, in a solvent, such as acetone or dichloromethane, for example.

In a final stage, the carboxylic acids of general formula (VI) can be prepared by oxidation of the aldehydes of formula (XVIII) with sodium perchlorite in a mixture of solvents, such as water and tert-butanol.

The peracid of formula (IV) can be prepared according to Reaction Scheme 11.

Scheme 11

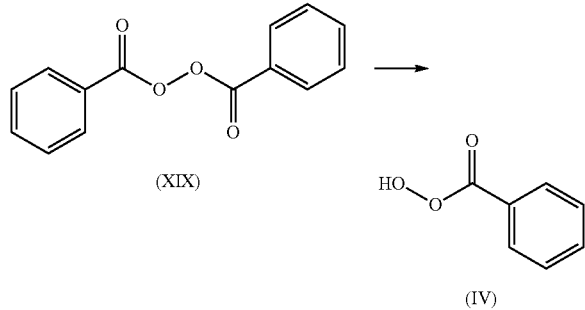

(XIX) → (IV)

According to Scheme 11, the peracid of formula (IV) is prepared from dibenzoyl peroxide (XIX) by methods chosen from those known to a person skilled in the art (U.S. Pat. No. 3,075,921). They comprise the use of dibenzoyl peroxide (XIX) and of sodium in a mixture of solvents, such as methanol and chloroform.

The peracids of formula (IX) can be prepared according to Reaction Scheme 12.

Scheme 12

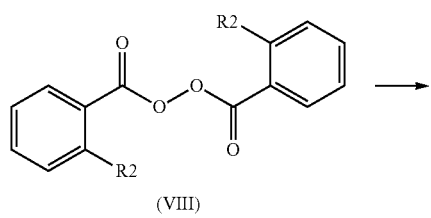

(VIII)

According to Scheme 12, the peracids of formula (IX) are prepared from the peroxide of formula (VIII) by methods chosen from those known to a person skilled in the art (U.S. Pat. No. 3,075,921). They comprise the use of a peroxide (VIII) and of sodium in a mixture of solvents, such as methanol and chloroform.

Study of the Sensitivity of the Peroxides to *Propionibacterium acnes*

Principle of the test: the aim is to evaluate the antibacterial activity of the peroxides by measuring the Minimum Inhibitory Concentrations (MICs). The MIC is defined as the lowest concentration of product capable of inhibiting all visible growth.

Microbial Strain and Origin:

The study of the sensitivity of the products is carried out on a strain from the Collection de l'Institut Pasteur (CIP) of *Propionibacterium acnes* (*P. acnes*): *P. acnes* CIP53.117, equivalent ATCC6919, origin: acne facial lesion (1920), source CRBIP, Institut Pasteur, Paris.

Test on the Products:

The products are dissolved at 1280 mg/l in an absolute ethanol/sterile Tween 80/sterile Wilkins-Chalgren broth mixture (May 10, 1985 v/v/v). The dilution ranges produced are an adaptation of the method described by the CLSI for methods of diluting in a liquid medium. The range is composed of 10 concentrations from 2.5 mg/l to 1280 mg/l with an interval of ratio 2.

The suspension of *P. acnes* is prepared in Wilkins-Chalgren broth and is calibrated at an optical density of approximately 0.4 at a wavelength 525 nm. It is subsequently diluted to $1/10^{th}$ in Wilkins-Chalgren broth and then dispensed into the test wells so as to obtain a final suspension of approximately $10^5$-$10^6$ cfu/ml in each test well.

The solutions of the test products are distributed on a 96-well microplate and incubated at 36° C.±2° C. under an anaerobic atmosphere for a time of at least 72 h. The first well for which there is no growth visible to the naked eye is regarded as the MIC.

| Example No. | MIC in mg/l |
|---|---|
| 1 | 80 |
| 2 | 40 |
| 3 | 160 |
| 4 | 160 |
| 5 | 40 |
| 6 | 80 |
| 7 | N.T. |
| 8 | 320 |
| 9 | 320 |
| 10 | 80 |
| 11 | 320 |
| 12 | 320 |

NT: Not tested

Evaluation of the Anti-Inflammatory Activity of the Peroxides after a Single Topical Administration in TPA-Induced Ear Oedema.

Principle of the Test:

the aim is to evaluate the anti-inflammatory activity of the peroxides by measuring the thickness of mouse ear after TPA topical application. The anti-inflammatory activity is defined as a inhibition percentage of the TAP-induced ear oedema.

The objective of the study was to demonstrate the anti-inflammatory effect of New peroxide in comparison to BPO (Benzoyl peroxide).

Test on the Products:

An oedema was induced by a single topical application of 20 μl of TPA dissolved in acetone at 0.01%.

Then a single topical application of tested compounds dissolved in TPA solution.

Method of Evaluation:

Ear thickness was measured at T6 h.

Results are expressed in percentages based on the inhibition on the oedema induced by the TPA application.

Benzoyl peroxide (BPo) was tested 2 times as a reference peroxide.

|  | Ear oedema | | Inhibition |
| --- | --- | --- | --- |
|  | Mean | Sem | vs TPA (%) |
| TPA 0.01% | 28.80 | 1.67 | N/A |
| TPA 0.01% + BPO 5% | 17.60 | 4.45 | 21.4 |
| TPA 0.01% + BPO 5% | 20.80 | 2.59 | 27.8 |
| TPA 0.01% + Ex1 1% | 24.80 | 1.79 | 13.9 |
| TPA 0.01% + Ex1 2.5% | 20.20 | 2.09 | 29.9 |
| TPA 0.01% + Ex1 5% | 13.40 | 0.40 | 53.5 |
| TPA 0.01% + Ex3 1% | 13.80 | 3.68 | 45.7 |
| TPA 0.01% + Ex3 2.5% | 8.60 | 1.50 | 66.1 |
| TPA 0.01% + Ex3 5% | 4.80 | 1.66 | 81.1 |
| TPA 0.01% + Ex5 1% | 20.40 | 2.93 | 8.9 |
| TPA 0.01% + Ex5 2.5% | 12.40 | 2.42 | 44.6 |
| TPA 0.01% + Ex5 5% | 6.20 | 0.97 | 72.3 |
| TPA 0.01% + Ex6 1% | 9.60 | 1.17 | 57.1 |
| TPA 0.01% + Ex6 2.5% | 4.80 | 1.56 | 78.6 |
| TPA 0.01% + Ex6 5% | 1.40 | 0.40 | 93.8 |

Conclusion:

The aim of this study was to demonstrate the anti-inflammatory effect of New peroxides after a single topical application in the TPA-induced ear oedema mouse model.

Ex1 at 1%, 2.5% and 5% showed a dose-dependent anti-inflammatory effect. At 5% the activity was significantly superior to that produced by BPO 5%.

Ex3 showed a strong dose-dependent anti-inflammatory effect

Ex5 at 5% showed a significant anti-inflammatory effect.

Ex6 showed a strong dose-dependent anti-inflammatory effect.

When compared to BPO at 5%, Ex5 and Ex6 demonstrate a stronger anti-inflammatory effect.

EXAMPLE (2-(Ethoxycarbonyloxy)benzoyl)benzoyl peroxide 1-1: 2-(ethoxycarbonyloxy)benzoic acid 60 g (434 mmol) of salicylic acid and 111 ml of N,N-dimethylaniline are dissolved in 360 ml of toluene. The medium is cooled to 0° C. and then 41.5 ml (434 mmol) of ethyl chloroformate are added dropwise. After stirring for 2 hours at ambient temperature, the mixture is washed with a 1N aqueous hydrochloric acid solution and then with a saturated sodium chloride solution. The organic phase is dried over magnesium sulphate, filtered and concentrated. The residue is taken up in dichloromethane and precipitated from heptane. The solid is filtered off and then dried. 38 g of 2-(ethoxycarbonyloxy)benzoic acid are obtained in the form of a white solid with a yield of 42%.

1-2: 2-(ethoxycarbonyloxy)benzoyl chloride 5.9 g (28 mmol) of 2-(ethoxycarbonyloxy)benzoic acid are dissolved in 30 ml of toluene with a few drops of pyridine. 2.15 ml (29 mmol) of thionyl chloride are added dropwise and the mixture is stirred at ambient temperature for 18 h and then concentrated to dryness. The residue is precipitated from pentane. The solid is filtered off and then dried. 5.2 g of 2-(ethoxycarbonyloxy)benzoyl chloride are obtained in the form of a white solid with a yield of 80%.

1-3: benzenecarboperoxoic acid 19 g (78 mmol) of dibenzoyl peroxide are dissolved in 125 ml of chloroform at −5° C. 2.2 g (94 mmol) of sodium dissolved in 50 ml of methanol under a stream of nitrogen are added dropwise. After stirring at −5° C. for 30 minutes, ice-cold water is added and the medium is acidified with a 2N aqueous hydrochloric acid solution. Extraction with dichloromethane is carried out and then the organic phase is dried over magnesium sulphate, filtered and concentrated. 9 g of benzenecarboperoxoic acid are obtained in the form of a white solid with a yield of 83%.

1-4: 2-(ethoxycarbonyloxy)benzoyl)benzoyl peroxide 8.6 g (67 mmol) of 2-(ethoxycarbonyloxy)benzoyl chloride (obtained in Example 1.2) and 10.2 g (44 mmol) of benzenecarboperoxoic acid are dissolved in 43 ml of chloroform. The mixture is cooled to −18° C. and then 2.2 ml (38 mmol) of pyridine in 5 ml of dichloromethane are added dropwise. After stirring at −18° C. for 2 hours, water is added and the mixture is extracted with dichloromethane. The organic phase is dried over magnesium sulphate, filtered and then concentrated. The residue is purified by chromatography on silica gel eluted with a pentane/dichloromethane 5/5 mixture. 11 g of (2-(ethoxycarbonyloxy)benzoyl)benzoyl peroxide are obtained in the form of a beige solid with a yield of 75%.

$^1$H NMR/CDCl$_3$: δ=1.32 (t, J=7.1 Hz, 3H); 4.29 (q, J=7.2 Hz, 2H); 7.22 (dd, J=1 Hz, J=7 Hz, 1H); 7.34 (td, J=1 Hz, J=8 Hz, 1H); 7.45 (t, J=8 Hz, 2H); 7.60 (m, 2H); 8.00 (m, 3H).

Example 2

(2-(tert-butoxycarbonyloxy)benzoyl)benzoyl peroxide 2-1: 2-(tert-butoxycarbonyloxy)benzaldehyde 350 mg (2.8 mmol) of N,N-dimethylaminopyridine and 8.1 ml (46.9 mmol) of N,N-diisopropylethylamine are added to a solution containing 20.9 g (95.7 mmol) of di(tert-butyl) dicarbonate in 150 ml of tetrahydrofuran under a stream of nitrogen. 10 ml (93.8 mmol) of salicylaldehyde are added dropwise. After stirring at ambient temperature for 2 hours, the medium is treated with a 1N aqueous hydrochloric acid solution and then extracted with a heptane/ethyl acetate 1/1 mixture. The organic phase is dried over magnesium sulphate, filtered and concentrated. 21.5 g of 2-(tert-butoxycarbonyloxy)benzaldehyde are obtained in the form of a yellow oil with a quantitative yield.

2-2: 2-(tert-butoxycarbonyloxy)benzoic acid 21.5 g (93.8 mmol) of 2-(tert-butoxycarbonyloxy)-benzaldehyde and 80 ml (750 mmol) of 2-methyl-2-butene are diluted in 250 ml of tert-butanol. A solution containing 28.1 g (234 mmol) of sodium hydrogenphosphate and 29.7 g (328 mmol) of sodium chlorite in 75 ml of water is added dropwise to the reaction medium, which is stirred at ambient temperature for 2 hours. The mixture is evaporated under reduced pressure and the residue is dissolved in dichloromethane. The organic phase is washed with water, dried over magnesium sulphate, filtered and concentrated. The white solid obtained is precipitated from heptane at 0° C. The precipitate is filtered off and then rinsed with heptane and dried. 15.8 g of 2-(tert-butoxycarbonyloxy)benzoic acid are obtained in the form of a white powder with a yield of 70%.

2-3: (2-(tert-butoxycarbonyloxy)benzoyl)benzoyl peroxide 3 g (13 mmol) of 2-(tert-butoxycarbonyloxy)benzoic acid and 1.8 g (13 mmol) of benzenecarboperoxoic acid (prepared as described in Example 1-3) are dissolved in a diethyl ether/dichloromethane 6/4 mixture. The solution is cooled to 0° C. and then 2.6 g (13 mmol) of N,N'-dicyclohexylcarbodiimide dissolved in 50 ml of diethyl ether are added dropwise. After stirring at 0° C. for 3 hours, the reaction medium is filtered and then concentrated to dryness. The residue is purified by chromatography on silica gel eluted with a pentane/dichloromethane 4/6 mixture. 2.2 g of (2-(tert-butoxycarbonyloxy)benzoyl)benzoyl peroxide are obtained in the form of a white solid with a yield of 49%.

$^1$H NMR/CDCl$_3$: δ=1.57 (s, 9H); 7.29 (dd, J=0.9 Hz, J=8 Hz, 1H); 7.40 (td, J=1 Hz, J=7.7 Hz, 1H); 7.52 (t, J=7.5 Hz, 2H); 7.68 (t, J=7.6 Hz, 2H); 8.07 (dd, J=1.3 Hz, J=7.4 Hz, 3H).

Example 3 bis(2-(ethoxycarbonyloxy)benzoyl)peroxide 3-1: bis(2-(ethoxycarbonyloxy)benzoyl)peroxide 5.2 g (23 mmol) of 2-(ethoxycarbonyloxy)benzoyl chloride (prepared as described in Example 1-2) are dissolved in 26 ml of tetrahydrofuran under a stream of nitrogen with 2.4 g (23 mmol) of sodium bicarbonate. The mixture is cooled to −15° C. and then 0.7 ml (12.4 mmol) of 50% aqueous hydrogen peroxide are added dropwise. After stirring at 0° C. for 4 h, ice-cold water is added to the medium and then extraction is carried out with diethyl ether. The organic phase is dried over magnesium sulphate, filtered and concentrated to dryness. The residue is purified by chromatography on silica gel eluted with a cyclohexane/dichloromethane 3/7 mixture. 2.1 g of bis(2-(ethoxycarbonyloxy)benzoyl)peroxide are obtained in the form of a white solid with a yield of 45%.

$^1$H NMR/CDCl$_3$: δ=1.32 (t, J=7.1 Hz, 6H); 4.28 (q, J=7.2 Hz, 4H); 7.24 (dd, J=1 Hz, J=8 Hz, 2H); 7.33 (td, J=1 Hz, J=7.7 Hz, 2H); 7.61 (td, J=1.7 Hz, J=7.6 Hz, 2H); 7.98 (dd, J=1.7 Hz, J=7.8 Hz, 2H).

Example 4 bis(2-(tert-butoxycarbonyloxy)benzoyl)peroxide 4-1: bis(2-(tert-butoxycarbonyloxy)benzoyl)peroxide 3.5 g (17 mmol) of N,N'-dicyclohexylcarbodiimide are dissolved in 40 ml of diethyl ether at −18° C. 2.4 ml (42 mmol) of an aqueous hydrogen peroxide solution are added and also 4 g (17 mmol) of 2-(tert-butoxycarbonyloxy)benzoic acid (prepared as described in Example 2-2) dissolved in 30 ml of dichloromethane. After stirring at −18° C. for 5 hours, 50 ml of diethyl ether are added, the reaction medium is filtered and then concentrated, and the solid obtained is precipitated from a diethyl ether/pentane 2/8 mixture, filtered off and then dried. 2.2 g of bis(2-(tert-butoxycarbonyloxy)benzoyl)peroxide are obtained in the form of a white solid with a yield of 28%.

$^1$H NMR/CDCl$_3$: δ=1.57 (s, 18H); 7.31 (d, J=1 Hz, J=8.2 Hz, 2H); 7.39 (td, J=1.1 Hz, J=8 Hz, 2H); 7.68 (td, J=1.7 Hz, J=7.6 Hz, 2H); 8.04 (dd, J=1.6 Hz, J=7.8 Hz, 2H).

Example 5

(2-(isopropoxycarbonyloxy)benzoyl)benzoyl peroxide 5-1: 2-(isopropoxycarbonyloxy)benzaldehyde 26 ml (190 mmol) of triethylamine and then 185 ml (190 mmol) of a 1M solution of isopropyl chloroformate in toluene are added dropwise to a solution containing 15 g (120 mmol) of salicylaldehyde in 150 ml of tetrahydrofuran at 0° C. The mixture is stirred at 0° C. for 2 hours and then at ambient temperature for 18 hours. Water is added and the reaction medium is extracted with ethyl acetate. The organic phase is washed with water, dried over magnesium sulphate, filtered and concentrated. 27 g of 2-(isopropoxy-carbonyloxy)benzaldehyde are obtained in the form of a yellow oil with a quantitative yield.

5-2: 2-(isopropoxycarbonyloxy)benzoic acid

Analogously to Example 2-2, 9 g of 2-(isopropoxy-carbonyloxy)benzoic acid are obtained, from 15 g (72 mmol) of 2-(isopropoxycarbonyloxy)benzaldehyde, in the form of a white solid with a yield of 56%.

5-3: 2-(isopropoxycarbonyloxy)benzoyl chloride 5 g (22 mmol) of 2-(isopropoxycarbonyloxy)benzoic acid are dissolved in 50 ml of dichloromethane with a few drops of pyridine. 1.95 ml (27 mmol) of thionyl chloride are added dropwise and the mixture is stirred at ambient temperature for 18 h and then concentrated to dryness. 5.7 g of 2-(isopropoxycarbonyloxy)benzoyl chloride are obtained with a quantitative yield.

5-4: (2-(isopropoxycarbonyloxy)benzoyl)benzoyl peroxide

Analogously to Example 1-4, 3.7 g of (2-(isopropoxycarbonyloxy)benzoyl)benzoyl peroxide are obtained, from 5.4 g (22 mmol) of 2-(chlorocarbonyl)phenyl isopropyl carbonate and 4.6 g (33 mmol) of benzenecarboperoxoic acid (prepared as described in Example 1-3), in the form of a white solid with a yield of 49%.

$^1$H NMR/CDCl$_3$: δ=1.40 (d, J=6.2 Hz, 6H); 5.03 (q, J=6.2 Hz, 1H); 7.32 (d, J=8.2 Hz, 1H); 7.41 (t, J=7.7 Hz, 1H); 7.53 (m, 2H); 7.70 (m, 2H); 8.08 (m, 3H).

Example 6 bis(2-(isopropoxycarbonyloxy)benzoyl)peroxide 6-1: bis(2-(isopropoxycarbonyloxy)benzoyl)peroxide Analogously to Example 4-1, 1.48 g of bis(2-(isopropoxycarbonyloxy)benzoyl)peroxide are obtained, from 3.6 g (16 mmol) of 2-(isopropoxycarbonyl-oxy)benzoic acid, in the form of a white solid with a yield of 41%.
$^1$H NMR/CDCl$_3$: δ=1.40 (d, J=6.2 Hz, 12H); 5.03 (q, J=6.2 Hz, 2H); 7.23 (dd, J=8.2 Hz, J=1 Hz, 2H); 7.32 (td, J=7.6 Hz, J=1 Hz, 2H); 7.59 (td, J=7.6 Hz, J=1.7 Hz, 2H); 7.96 (dd, J=7.8 Hz, J=1.7 Hz, 2H).

Example 7

(2-(cyclohexyloxycarbonyloxy)benzoyl)benzoyl peroxide 7-1: 2-(cyclohexyloxycarbonyloxy)benzaldehyde 6.3 ml (45 mmol) of triethylamine and then 7.4 g (45 mmol) of cyclohexyl chloroformate are added dropwise to a solution containing 5 g (41 mmol) of salicylaldehyde in 50 ml of tetrahydrofuran at 0° C. After stirring at ambient temperature for 2 hours, the medium is treated with water and then extracted with a heptane/ethyl acetate 1/1 mixture. The organic phase is dried over magnesium sulphate, filtered and concentrated. 10.3 g of 2-(cyclohexyloxycarbonyl-oxy)benzaldehyde are obtained in the form of a yellow oil with a quantitative yield.

7-2: 2-(cyclohexyloxycarbonyloxy)benzoic acid

Analogously to Example 2-2, 8.5 g of 2-(cyclohexyloxycarbonyloxy)benzoic acid are obtained, from 10.3 g (41 mmol) of cyclohexyl 2-formylphenyl carbonate, in the form of a white solid with a yield of 78%.

7-3: (2-(cyclohexyloxycarbonyloxy)benzoyl)benzoyl peroxide

Analogously to Example 2-3, 4 g of (2-(cyclo-hexyloxycarbonyloxy)benzoyl)benzoyl peroxide are obtained, from 4.2 g (16 mmol) of 2-(cyclohexyloxycarbonyloxy)benzoic acid, in the form of an orange oil with a yield of 65%.
$^1$H NMR/CDCl$_3$: δ=1.30 (m, 3H); 1.55 (m, 3H); 1.77 (m, 2H); 1.98 (m, 2H); 4.79 (m, 1H); 7.29 (m, 1H); 7.40 (t, J=8 Hz, 1H); 7.53 (m, 2H); 7.66 (m, 2H), 8.07 (m, 3H).

Example 8 bis(2-(cyclohexyloxycarbonyloxy)benzoyl)peroxide 8-1: bis(2-(cyclohexyloxycarbonyloxy)benzoyl)peroxide Analogously to Example 4-1, 2.4 g of bis(2-(cyclohexyloxycarbonyloxy)benzoyl)peroxide are obtained, from 4 g (15.1 mmol) of 2-(cyclohexyloxycarbonyloxy)benzoic acid (prepared as described in Example 7-2), in the form of a white solid with a yield of 60%.

$^1$H NMR/CDCl$_3$: δ=1.25 (m, 6H); 1.49 (m, 6H); 1.53 (m, 4H); 1.90 (m, 4H); 4.67 (m, 2H); 7.23 (dd, J=1 Hz, J=8.2 Hz, 2H); 7.32 (td, J=1 Hz, J=7.7 Hz, 2H); 7.59 (td, J=1.7 Hz, J=7.7 Hz, 2H); 7.97 (dd, J=1.7 Hz, J=7.8 Hz, 2H).

Example 9

(2-(tert-butyryloxy)benzoyl)benzoyl peroxide 9-1: 2-(2,2-dimethylpropionyloxy)benzoic acid 10 g (72.4 mmol) of salicylic acid and 6.1 ml (76 mmol) of pyridine are placed in 100 ml of acetone at −5° C. 9.3 ml (76 mmol) of 2,2-dimethylpropionyl chloride are added and, after stirring at ambient temperature for 2 hours, water is added and the mixture is extracted with dichloromethane. The organic phase is dried over magnesium sulphate, filtered and concentrated. The residue is precipitated from heptane at 0° C. and then filtered off. 16.9 g of 2-(2,2-dimethylpropionyloxy)benzoic acid are obtained in the form of a white powder with a yield of 95%.

9-2: 2-(chlorocarbonyl)phenyl 2,2-dimethylpropanoate 6 g (27 mmol) of 2-(2,2-dimethylpropionyl-oxy)benzoic acid are dissolved in 60 ml of dichloromethane with a few drops of pyridine. 2.4 ml (32 mmol) of thionyl chloride are added dropwise and the mixture is stirred at ambient temperature for 18 h and then concentrated to dryness. 6.8 g of 2-(chlorocarbonyl)phenyl 2,2-dimethylpropanoate are obtained in a quantitative yield.

9-3: (2-(tert-butyryloxy)benzoyl)benzoyl peroxide

Analogously to Example 1-4, 1.5 g of (2-(tert-butyryloxy)benzoyl)benzoyl peroxide are obtained, from 4.1 g (17 mmol) of 2-(chlorocarbonyl)phenyl 2,2-dimethylpropanoate and 3.5 g (26 mmol) of benzenecarboperoxoic acid (prepared as described in Example 1-3), in the form of an orange oil with a yield of 25%.
$^1$H NMR/CDCl$_3$: δ=1.40 (s, 9H); 7.20 (d, J=6 Hz, 1H); 7.37 Hz (t, J=7.5 Hz, 1H); 7.53 (t, J=7.5 Hz, 2H); 7.66 (m, 2H); 8.05 (m, 3H).

Example 10

(2-(isobutyryloxy)benzoyl)benzoyl peroxide 10-1: 2-(isobutyryloxy)benzoic acid

Analogously to Example 9-1, 13.4 g of 2-(isobutyryloxy)benzoic acid are obtained, from 10 g (72.4 mmol) of salicylic acid, 6.1 ml (76 mmol) of pyridine and 8 ml (76 mmol) of isobutyryl chloride, in the form of a white powder with a yield of 88%.

10-2: 2-(chlorocarbonyl)phenyl isobutyrate

Analogously to Example 9-2, 5 g of 2-(chlorocarbonyl)phenyl isobutyrate are obtained, from 5 g (24 mmol) of 2-(isobutyryloxy)benzoic acid, in the form of a colourless oil with a yield of 92%.

10-3: (2-(isobutyryloxy)benzoyl)benzoyl peroxide

Analogously to Example 1-4, 1.9 g of (2-(isobutyryloxy)benzoyl)benzoyl peroxide are obtained, from 5 g (22 mmol)

of 2-(chlorocarbonyl)phenyl isobutyrate and 6 g (44 mmol) of benzenecarboperoxoic acid (prepared as described in Example 1-3), in the form of an orange oil with a yield of 26%.

$^1$H NMR/CDCl$_3$: δ=1.28 (d, J=6 Hz, 6H); 7.11 (d, J=9 Hz, 1H); 7.31 Hz (t, J=9 Hz, 1H); 7.44 (t, J=7.5 Hz, 2H); 7.59 (m, 2H); 8.00 (m, 3H).

Example 11

(2-(cyclohexanecarbonyloxy)benzoyl)benzoyl peroxide 11-1: 2-(cyclohexanecarbonyloxy)benzoic acid Analogously to Example 9-1, 16.6 g of 2-(cyclohexanecarbonyloxy)benzoic acid are obtained, from 10 g (72.4 mmol) of salicylic acid, 6.1 ml (76 mmol) of pyridine and 10.2 ml (76 mmol) of cyclohexylacetyl chloride, in the form of a white powder with a yield of 92%.

11-2: 2-(chlorocarbonyl)phenyl cyclohexanecarboxylate

Analogously to Example 9-2, 5.9 g of 2-(chlorocarbonyl)phenyl cyclohexanecarboxylate are obtained, from 6 g (24 mmol) of 2-(cyclohexanecarbonyloxy)benzoic acid, in the form of a colourless oil with a yield of 91%.

11-3: (2-(cyclohexanecarbonyloxy)benzoyl)benzoyl peroxide

Analogously to Example 1-4, 3 g of (2-(cyclohexanecarbonyloxy)benzoyl)benzoyl peroxide are obtained, from 5.9 g (22 mmol) of 2-(chlorocarbonyl)phenyl cyclohexanecarboxylate and 4.5 g (33 mmol) of benzenecarboperoxoic acid (prepared as described in Example 1-3), in the form of a white powder with a yield of 36%.

$^1$H NMR/CDCl$_3$: δ=1.31 (m, 3H); 1.57 (m, 3H); 1.83 (m, 2H); 2.12 (m, 2H); 2.68 (m, 1H); 7.20 (dd, J=1 Hz, J=8 Hz, 1H); 7.39 (td, J=1 Hz, J=7.7 Hz, 1H); 7.54 (m, 2H); 7.68 (m, 2H); 8.09 (m, 3H).

Example 12

[2-(2-(adamantan-1-yl)acetoxy)benzoyl]benzoyl peroxide 12-1: 2-(2-(adamantan-1-yl)acetoxy)benzoic acid Analogously to Example 9-1, 17.2 g of 2-(2-(adamantan-1-yl)acetoxy)benzoic acid are obtained, from 9.3 g (67.3 mmol) of salicylic acid, 5.7 ml (76 mmol) of pyridine and 15 g (76 mmol) of 1-adamantanecarbonyl chloride, in the form of a white powder with a yield of 81%.

12-2: 2-(chlorocarbonyl)phenyl(adamantan-1-yl)acetate

Analogously to Example 9-2, 5.8 g of 2-(chlorocarbonyl)phenyl(adamantan-1-yl)acetate are obtained, from 5 g (16 mmol) of 2-(2-(adamantan-1-yl)acetoxy)-benzoic acid, in the form of a white solid with a quantitative yield.

12-3: [2-(2-(adamantan-1-yl)acetoxy)benzoyl]benzoyl peroxide

Analogously to Example 1-4, 1.9 g of [2-(2-(adamantan-1-yl)acetoxy)benzoyl]benzoyl peroxide are obtained, from 6.36 g (19 mmol) of 2-(chlorocarbonyl)phenyl(adamantan-1-yl)acetate and 4 g (29 mmol) of benzenecarboperoxoic acid (prepared as described in Example 1-3), in the form of a white powder with a yield of 22%.

$^1$H NMR/CDCl$_3$: δ=1.76 (m, 12H); 2.01 (1, 3H); 2.43 (s, 2H); 7.22 (dd, J=1 Hz, J=8 Hz, 1H); 7.39 (td, J=1 Hz, J=7.7 Hz, 1H); 7.55 (m, 2H); 7.68 (m, 2H); 8.06 (m, 3H).

The invention claimed is:

1. A compound of following formula (I):

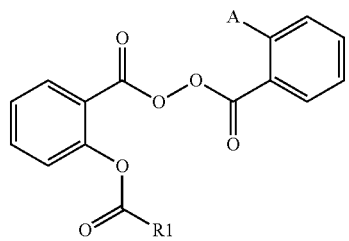

in which:

R1 represents a lower alkyl, a higher alkyl, a cycloalkyl, a cycloalkylalkyl, a lower alkoxy, a higher alkoxy, a cycloalkyloxy, a cycloalkylalkoxy, an aryl, an aryloxy or a mono- or dialkylamino;

A represents a hydrogen or the following sequence;

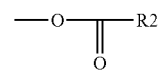

R2 represents a lower alkoxy, a higher alkoxy, a cycloalkyloxy, a cycloalkylalkoxy, an aryloxy or a mono- or dialkylamino; and wherein said lower alkyl is a saturated, linear or branched hydrocarbon chain comprising from 2 to 4 carbon atoms.

2. The compound as defined by claim 1 wherein, a. R1 represents a lower alkyl, a cycloalkyl, a cycloalkylalkyl, a lower alkoxy, a cycloalkyloxy or a mono- or dialkylamino;

b. A represents a hydrogen or a defined group of such type:

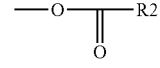

c. R2 represents a lower alkoxy, a cycloalkyloxy or a mono- or dialkylamino.

3. The compound as defined by claim 1, wherein:

a. R1 represents a lower alkyl, a cycloalkyl, a cycloalkylalkyl, a lower alkoxy or a cycloalkyloxy;

b. A represents a hydrogen or a defined group of such type:

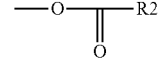

c. R2 represents a lower alkoxy or a cycloalkyloxy.

4. The compound as defined by claim 1, wherein the compound is selected from the group consisting of:

(2-(Ethoxycarbonyloxy)benzoyl)benzoyl peroxide;
(2-(tert-Butoxycarbonyloxy)benzoyl)benzoyl peroxide;
Bis(2-(ethoxycarbonyloxy)benzoyl)peroxide;

Bis(2-(tert-butoxycarbonyloxy)benzoyl)peroxide;
(2-(isopropoxycarbonyloxy)benzoyl)benzoyl peroxide;
Bis(2-(isopropoxycarbonyloxy)benzoyl)peroxide;
(2-(Cyclohexyloxycarbonyloxy)benzoyl)benzoyl peroxide;
Bis(2-(cyclohexyloxycarbonyloxy)benzoyl)peroxide;
(2-(tert-Butyryloxy)benzoyl)benzoyl peroxide;
(2-(Isobutyryloxy)benzoyl)benzoyl peroxide;
(2-(Cyclohexanecarbonyloxy)benzoyl)benzoyl peroxide;
[2-(2-(Adamantan-1-yl)acetoxy)benzoyl]benzoyl peroxide;
[2-(Adamentene-1-carbonyloxy)benzoyl]benzoyl peroxide;
(2-(Phenoxycarbonyloxy)benzoyl)benzoyl peroxide;
(2-(Methoxycarbonyloxy)benzoyl)benzoyl peroxide;
(2-(Propoxycarbonyloxy)benzoyl)benzoyl peroxide;
(2-(Butoxycarbonyloxy)benzoyl)benzoyl peroxide;
(2-(sec-Butoxycarbonyloxy)benzoyl)benzoyl peroxide;
(2-(Isobutoxycarbonyloxy)benzoyl)benzoyl peroxide;
(2-(Propionyloxy)benzoyl)benzoyl peroxide;
(2-(Butyryloxy)benzoyl)benzoyl peroxide;
(2-(Pentanoyloxy)benzoyl)benzoyl peroxide;
[2-(3-Methylbutyryloxy)benzoyl]benzoyl peroxide;
[2-(2-Methylbutyryloxy)benzoyl]benzoyl peroxide;
(2-(Cyclopropanecarbonyloxy)benzoyl)benzoyl peroxide;
(2-(Cyclobutanecarbonyloxy)benzoyl)benzoyl peroxide;
(2-(Cyclopentanecarbonyloxy)benzoyl)benzoyl peroxide;
(2-(Benzoyloxy)benzoyl)benzoyl peroxide;
(2-(Dimethylcarbamoyloxy)benzoyl)benzoyl peroxide;
(2-(Diethylcarbamoyloxy)benzoyl)benzoyl peroxide;
(2-(Methylcarbamoyloxy)benzoyl)benzoyl peroxide;
(2-(Ethylcarbamoyloxy)benzoyl)benzoyl peroxide;
(2-(Isopropylcarbamoyloxy)benzoyl)benzoyl peroxide;
(2-(Propylcarbamoyloxy)benzoyl)benzoyl peroxide;
[2-((Isopropyl)(methyl)carbamoyloxy)benzoyl]benzoyl peroxide;
[2-((Ethyl)(isopropyl)carbamoyloxy)benzoyl]benzoyl peroxide;
(2-(Hexanoyloxy)benzoyl)benzoyl peroxide;
(2-(Heptanoyloxy)benzoyl)benzoyl peroxide;
(2-(Octanoyloxy)benzoyl)benzoyl peroxide;
(2-(Nonanoyloxy)benzoyl)benzoyl peroxide;
[2-(2-Ethylbutyryloxy)benzoyl]benzoyl peroxide;
[2-(3,3-Dimethylbutyryloxy)benzoyl]benzoyl peroxide;
(2-(Pentyloxycarbonyloxy)benzoyl)benzoyl peroxide;
(2-(Hexyloxycarbonyloxy)benzoyl)benzoyl peroxide;
(2-(Heptyloxycarbonyloxy)benzoyl)benzoyl peroxide;
(2-(Octyloxycarbonyloxy)benzoyl)benzoyl peroxide;
[2-(1-Ethylpropoxycarbonyloxy)benzoyl]benzoyl peroxide;
[2-(2,2-Dimethylpropoxycarbonyloxy)benzoyl]benzoyl peroxide;
Bis(2-(phenoxycarbonyloxy)benzoyl)peroxide;
Bis(2-(methoxycarbonyloxy)benzoyl)peroxide;
Bis(2-(propoxycarbonyloxy)benzoyl)peroxide;
Bis(2-(butoxycarbonyloxy)benzoyl)peroxide;
Bis[2-(3-methylbutyryloxy)benzoyl]peroxide;
Bis[2-(2-methylbutyryloxy)benzoyl]peroxide;
Bis(2-(dimethylcarbamoyloxy)benzoyl)peroxide;
Bis(2-(diethylcarbamoyloxy)benzoyl)peroxide;
Bis(2-(methylcarbamoyloxy)benzoyl)peroxide;
Bis(2-(ethylcarbamoyloxy)benzoyl)peroxide;
Bis(2-(isopropylcarbamoyloxy)benzoyl)peroxide;
Bis(2-propylcarbamoyloxy)benzoyl)peroxide;
Bis(2-((isopropyl)(methyl)carbamoyloxy)benzoyl)peroxide;
Bis(2-((ethyl)(isopropyl)carbamoyloxy)benzoyl)peroxide;
Bis(2-(pentyloxycarbonyloxy)benzoyl)peroxide;
Bis(2-(hexyloxycarbonyloxy)benzoyl)peroxide;
Bis(2-(heptyloxycarbonyloxy)benzoyl)peroxide;
Bis(2-(octyloxycarbonyloxy)benzoyl)peroxide;
Bis[2-(1-ethylpropoxycarbonyloxy)benzoyl]peroxide;
Bis[2-(2,2-dimethylpropoxycarbonyloxy)benzoyl]peroxide;
(2-(Methoxycarbonyloxy)benzoyl)2-(isobutyryloxy)benzoyl peroxide;
(2-(Methoxycarbonyloxy)benzoyl)2-(tert-butyryloxy)benzoyl peroxide;
(2-(Methoxycarbonyloxy)benzoyl)2-(cyclohexanecarbonyloxy)benzoyl peroxide;
(2-(Methoxycarbonyloxy)benzoyl)2-(methylcarbamoyloxy)benzoyl peroxide;
(2-(Methoxycarbonyloxy)benzoyl)2-(dimethylcarbamoyloxy)benzoyl peroxide;
(2-(Ethoxycarbonyloxy)benzoyl)2-(isobutyryloxy)benzoyl peroxide;
(2-(Ethoxycarbonyloxy)benzoyl)2-(tert-butyryloxy)benzoyl peroxide;
(2-(Ethoxycarbonyloxy)benzoyl)2-(cyclohexanecarbonyloxy)benzoyl peroxide;
(2-(Ethoxycarbonyloxy)benzoyl)2-(methylcarbamoyloxy)benzoyl peroxide;
(2-(Ethoxycarbonyloxy)benzoyl)2-(dimethylcarbamoyloxy)benzoyl peroxide;
(2-(Isopropoxycarbonyloxy)benzoyl)2-(isobutyryloxy)benzoyl peroxide;
(2-(Isopropoxycarbonyloxy)benzoyl)2-(tert-butyryloxy)benzoyl peroxide:
(2-(Isopropoxycarbonyloxy)benzoyl)2-(cyclohexanecarbonyloxy)benzoyl peroxide;
(2-(Isopropoxycarbonyloxy)benzoyl)2-(methylcarbamoyloxy)benzoyl peroxide;
(2-(Isopropoxycarbonyloxy)benzoyl)2-(dimethylcarbamoyloxy)benzoyl peroxide;
(2-(tert-Butoxycarbonyloxy)benzoyl)2-(isobutyryloxy)benzoyl peroxide;
(2-(tert-Butoxycarbonyloxy)benzoyl)2-(tert-butyryloxy)benzoyl peroxide;
(2-(tert-Butoxycarbonyloxy)benzoyl)2-(cyclohexanecarbonyloxy)benzoyl peroxide;
(2-(tert-Butoxycarbonyloxy)benzoyl)2-(methylcarbamoyloxy)benzoyl peroxide;
(2-(tert-Butoxycarbonyloxy)benzoyl)2-(dimethylcarbamoyloxy)benzoyl peroxide;
(2-(Cyclohexyloxycarbonyloxy)benzoyl)2-(isobutyryloxy)benzoyl peroxide;
(2-(Cyclohexyloxycarbonyloxy)benzoyl)2-(tert-butyryloxy)benzoyl peroxide;
(2-(Cyclohexyloxycarbonyloxy)benzoyl)2-(cyclohexanecarbonyloxy)benzoyl peroxide;
(2-(Cyclohexyloxycarbonyloxy)benzoyl)2-(methylcarbamoyloxy)benzoyl peroxide;
(2-(Cyclohexyloxycarbonyloxy)benzoyl)2-(dimethylcarbamoyloxy)benzoyl peroxide;
(2-(Ethoxycarbonyloxy)benzoyl)2-(isopropoxycarbonyloxy)benzoyl peroxide;
(2-(Ethoxycarbonyloxy)benzoyl)2-(tert-butoxycarbonyloxy)benzoyl peroxide;
(2-(Ethoxycarbonyloxy)benzoyl)2-(cyclohexyloxycarbonyloxy)benzoyl peroxide; and
(2-(tert-Butyryloxy)benzoyl)2-(cyclohexyloxycarbonyloxy)benzoyl peroxide.

5. The compound as defined by claim 1, wherein the compound is a medicament.

6. The compound as described in claim 1,
wherein the compound is effective to treat pathologies or disorders related to the presence of *Propionibacterium acnes*.

7. A cosmetic composition comprising an effective amount of the compound as defined in claim 1, wherein the effective amount of the compound inhibits proliferation of the pathogenic microorganisms involved in the development of an acne-type skin disorder.

8. The composition of claim 7, wherein in the compound:
a. R1 represents a lower alkyl, a cycloalkyl, a cycloalkylalkyl, a lower alkoxy, a cycloalkyloxy or a mono- or dialkylamino;
b. A represents a hydrogen or a defined group of such type:

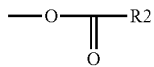

c. R2 represents a lower alkoxy, a cycloalkyloxy or a mono- or dialkylamino.

9. The composition of claim 7, wherein the compound is selected from the group consisting of:
(2-(Ethoxycarbonyloxy)benzoyl)benzoyl peroxide;
(2-(tert-Butoxycarbonyloxy)benzoyl)benzoyl peroxide;
Bis(2-(ethoxycarbonyloxy)benzoyl)peroxide;
Bis(2-(tert-butoxycarbonyloxy)benzoyl)peroxide;
(2-(Isopropoxycarbonyloxy)benzoyl)benzoyl peroxide;
Bis(2-(isopropoxycarbonyloxy)benzoyl)peroxide;
(2-(Cyclohexyloxycarbonyloxy)benzoyl)benzoyl peroxide;
Bis(2-(cyclohexyloxycarbonyloxy)benzoyl)peroxide;
(2-(tert-Butyryloxy)benzoyl)benzoyl peroxide;
(2-(Isobutyryloxy)benzoyl)benzoyl peroxide;
(2-(Cyclohexanecarbonyloxy)benzoyl)benzoyl peroxide;
[2-(2-(Adamantan-1-yl)acetoxy)benzoyl]benzoyl peroxide;
[2-(Adamentene-1-carbonyloxy)benzoyl]benzoyl peroxide;
(2-(Phenoxycarbonyloxy)benzoyl)benzoyl peroxide;
(2-(Methoxycarbonyloxy)benzoyl)benzoyl peroxide;
(2-(Propoxycarbonyloxy)benzoyl)benzoyl peroxide;
(2-(Butoxycarbonyloxy)benzoyl)benzoyl peroxide;
(2-(sec-Butoxycarbonyloxy)benzoyl)benzoyl peroxide;
(2-(Isobutoxycarbonyloxy)benzoyl)benzoyl peroxide;
(2-(Propionyloxy)benzoyl)benzoyl peroxide;
(2-(Butyryloxy)benzoyl)benzoyl peroxide;
(2-(Pentanoyloxy)benzoyl)benzoyl peroxide;
[2-(3-Methylbutyryloxy)benzoyl]benzoyl peroxide;
[2-(2-Methylbutyryloxy)benzoyl]benzoyl peroxide;
(2-(Cyclopropanecarbonyloxy)benzoyl)benzoyl peroxide;
(2-(Cyclobutanecarbonyloxy)benzoyl)benzoyl peroxide;
(2-(Cyclopentanecarbonyloxy)benzoyl)benzoyl peroxide;
(2-(Benzoyloxy)benzoyl)benzoyl peroxide;
(2-(Dimethylcarbamoyloxy)benzoyl)benzoyl peroxide;
(2-(Diethylcarbamoyloxy)benzoyl)benzoyl peroxide;
(2-(Methylcarbamoyloxy)benzoyl)benzoyl peroxide;
(2-(Ethylcarbamoyloxy)benzoyl)benzoyl peroxide;
(2-(Isopropylcarbamoyloxy)benzoyl)benzoyl peroxide;
(2-(Propylcarbamoyloxy)benzoyl)benzoyl peroxide;
[2-((Isopropyl)(methyl)carbamoyloxy)benzoyl]benzoyl peroxide;
[2-((Ethyl)(isopropyl)carbamoyloxy)benzoyl]benzoyl peroxide;
(2-(Hexanoyloxy)benzoyl)benzoyl peroxide;
(2-(Heptanoyloxy)benzoyl)benzoyl peroxide;
(2-(Octanoyloxy)benzoyl)benzoyl peroxide;
(2-(Nonanoyloxy)benzoyl)benzoyl peroxide;
[2-(2-Ethylbutyryloxy)benzoyl]benzoyl peroxide;
[2-(3,3-Dimethylbutyryloxy)benzoyl]benzoyl peroxide;
(2-(Pentyloxycarbonyloxy)benzoyl)benzoyl peroxide;
(2-(Hexyloxycarbonyloxy)benzoyl)benzoyl peroxide;
(2-(Heptyloxycarbonyloxy)benzoyl)benzoyl peroxide;
(2-(Octyloxycarbonyloxy)benzoyl)benzoyl peroxide;
[2-(1-Ethylpropoxycarbonyloxy)benzoyl]benzoyl peroxide;
[2-(2,2-Dimethylpropoxycarbonyloxy)benzoyl]benzoyl peroxide;
Bis(2-(phenoxycarbonyloxy)benzoyl)peroxide;
Bis(2-(methoxycarbonyloxy)benzoyl)peroxide;
Bis(2-(propoxycarbonyloxy)benzoyl)peroxide;
Bis(2-(butoxycarbonyloxy)benzoyl)peroxide;
Bis[2-(3-methylbutyryloxy)benzoyl]peroxide;
Bis[2-(2-methylbutyryloxy)benzoyl]peroxide;
Bis(2-(dimethylcarbamoyloxy)benzoyl)peroxide;
Bis(2-(diethylcarbamoyloxy)benzoyl)peroxide;
Bis(2-(methylcarbamoyloxy)benzoyl)peroxide;
Bis(2-(ethylcarbamoyloxy)benzoyl)peroxide;
Bis(2-(isopropylcarbamoyloxy)benzoyl)peroxide;
Bis(2-propylcarbamoyloxy)benzoyl)peroxide;
Bis(2-((isopropyl)(methyl)carbamoyloxy)benzoyl)peroxide;
Bis(2-((ethyl)(isopropyl)carbamoyloxy)benzoyl)peroxide;
Bis(2-(pentyloxycarbonyloxy)benzoyl)peroxide;
Bis(2-(hexyloxycarbonyloxy)benzoyl)peroxide;
Bis(2-(heptyloxycarbonyloxy)benzoyl)peroxide;
Bis(2-(octyloxycarbonyloxy)benzoyl)peroxide;
Bis[2-(1-ethylpropoxycarbonyloxy)benzoyl]peroxide;
Bis[2-(2,2-dimethylpropoxycarbonyloxy)benzoyl]peroxide;
(2-(Methoxycarbonyloxy)benzoyl)2-(isobutyryloxy)benzoyl peroxide;
(2-(Methoxycarbonyloxy)benzoyl)2-(tert-butyryloxy)benzoyl peroxide;
(2-(Methoxycarbonyloxy)benzoyl)2-(cyclohexanecarbonyloxy)benzoyl peroxide;
(2-(Methoxycarbonyloxy)benzoyl)2-(methylcarbamoyloxy)benzoyl peroxide;
(2-(Methoxycarbonyloxy)benzoyl)2-(dimethylcarbamoyloxy)benzoyl peroxide;
(2-(Ethoxycarbonyloxy)benzoyl)2-(isobutyryloxy)benzoyl peroxide;
(2-(Ethoxycarbonyloxy)benzoyl)2-(tert-butyryloxy)benzoyl peroxide;
(2-(Ethoxycarbonyloxy)benzoyl)2-(cyclohexanecarbonyloxy)benzoyl peroxide;
(2-(Ethoxycarbonyloxy)benzoyl)2-(methylcarbamoyloxy)benzoyl peroxide;
(2-(Ethoxycarbonyloxy)benzoyl)2-(dimethylcarbamoyloxy)benzoyl peroxide;
(2-(Isopropoxycarbonyloxy)benzoyl)2-(isobutyryloxy)benzoyl peroxide;
(2-(Isopropoxycarbonyloxy)benzoyl)2-(tert-butyryloxy)benzoyl peroxide;
(2-(Isopropoxycarbonyloxy)benzoyl)2-(cyclohexanecarbonyloxy)benzoyl peroxide;
(2-(Isopropoxycarbonyloxy)benzoyl)2-(methylcarbamoyloxy)benzoyl peroxide;
(2-(Isopropoxycarbonyloxy)benzoyl)2-(dimethylcarbamoyloxy)benzoyl peroxide;

(2-(tert-Butoxycarbonyloxy)benzoyl)2-(isobutyryloxy)benzoyl peroxide;
(2-(tert-Butoxycarbonyloxy)benzoyl)2-(tert-butyryloxy)benzoyl peroxide;
(2-(tert-Butoxycarbonyloxy)benzoyl)2-(cyclohexanecarbonyloxy)benzoyl peroxide;
(2-(tert-Butoxycarbonyloxy)benzoyl)2-(methylcarbamoyloxy)benzoyl peroxide;
(2-(tert-Butoxycarbonyloxy)benzoyl)2-(dimethylcarbamoyloxy)benzoyl peroxide;
(2-(Cyclohexyloxycarbonyloxy)benzoyl)2-(isobutyryloxy)benzoyl peroxide;
(2-(Cyclohexyloxycarbonyloxy)benzoyl)2-(tert-butyryloxy)benzoyl peroxide;
(2-(Cyclohexyloxycarbonyloxy)benzoyl)2-(cyclohexanecarbonyloxy)benzoyl peroxide;
(2-(Cyclohexyloxycarbonyloxy)benzoyl)2-(methylcarbamoyloxy)benzoyl peroxide;
(2-(Cyclohexyloxycarbonyloxy)benzoyl)2-(dimethylcarbamoyloxy)benzoyl peroxide;
(2-(Ethoxycarbonyloxy)benzoyl)2-(isopropoxycarbonyloxy)benzoyl peroxide;
(2-(Ethoxycarbonyloxy)benzoyl)2-(tert-butoxycarbonyloxy)benzoyl peroxide;
(2-(Ethoxycarbonyloxy)benzoyl)2-(cyclohexyloxycarbonyloxy)benzoyl peroxide; and
(2-(tert-Butyryloxy)benzoyl)2-(cyclohexyloxycarbonyloxy)benzoyl peroxide.

10. The composition of claim 7, wherein the acne-type skin disorder is *P. acnes*.

* * * * *